(12) United States Patent
Matsuura

(10) Patent No.: US 7,416,890 B2
(45) Date of Patent: Aug. 26, 2008

(54) BACULOVIRUS VECTOR, METHOD OF PRODUCING THEREOF AND METHOD OF GENE TRANSFER

(75) Inventor: Yoshiharu Matsuura, Suita (JP)

(73) Assignee: Osaka Industrial Promotion Organization, Osaka (JP)

( * ) Notice: Subject to any disclaimer, the term of this patent is extended or adjusted under 35 U.S.C. 154(b) by 0 days.

(21) Appl. No.: 11/086,372

(22) Filed: Mar. 23, 2005

(65) Prior Publication Data

US 2005/0208661 A1    Sep. 22, 2005

Related U.S. Application Data

(63) Continuation of application No. PCT/JP03/12275, filed on Sep. 25, 2003.

(30) Foreign Application Priority Data

Sep. 25, 2002   (JP)   ............... 2002-278469

(51) Int. Cl.
  C12N 15/63   (2006.01)
  C12N 15/64   (2006.01)
  C12N 15/866  (2006.01)
  A61K 48/00   (2006.01)

(52) U.S. Cl. .............. 435/456; 435/69.1; 435/455; 435/320.1

(58) Field of Classification Search ............... None
See application file for complete search history.

(56) References Cited

U.S. PATENT DOCUMENTS 5,750,383 A *  5/1998  Blissard et al. ............. 435/457
6,607,912 B2 * 8/2003  Blissard et al. ............ 435/320.1

FOREIGN PATENT DOCUMENTS

| WO | WO 98/11243 | 3/1998 |
|---|---|---|
| WO | WO 99/09193 | 2/1999 |
| WO | WO 00/77233 | 12/2000 |
| WO | WO 02/14527 | 2/2002 |
| WO | WO 02/072853 | 9/2002 |

OTHER PUBLICATIONS

Mangor et al., "A GP64-Null Baculovirus Pseudotyped with Vesicular Stomatitis Virus G Protein," 75 *J. Virol.* 2544-2556 (2001).
Oomens et al., "Requirement for GP64 to Drive Efficient Budding of *Autographa californica* Multicapsid Nucleopolyhedrovirus," 254 *Virology* 297-314 (1999).
Tani et al., "Characterization of Cell-Surface Determinants Important for Baculovirus Infection," 279 *Virology* 343-353 (2001).
Old et al., *Principles of Gene Manipulation* 335-338 (5th ed. 2000).
*Kitts et al., "A Method for Producing Recombinant Baculovirus Expression Vectors at High Frequency," 14 *Biotechniques* 810-817 (1993)(Partial Copy).
*Kitagawa et al., "Ligand-Directed Gene Targeting to Mammalian Cells by Pseudotype Baculoviruses," 79 *J. Virology* 3639-3652 (2005).
*Tani et al., "In Vitro and In Vivo Gene Delivery by Recombinant Baculoviruses," 77 *J. Virology* 9799-9808 (2003).
*Kost et al., "Recombinant Baculoviruses as Mammalian Cell Gene-Delivery Vectors," 20 *Trends in Biotechnology* 173-180 (2002).
Yee et al., Generation of High-Titer Pseudotyped Retroviral Vectors With Very Broad Host Range, 43A *Methods Cell Biol.* 99-112 (1994) (Abstract).

* cited by examiner

*Primary Examiner*—David Guzo
(74) *Attorney, Agent, or Firm*—James C. Lydon

(57) ABSTRACT

The present invention provides a novel baculovirus vector which can provide a desired protein not requiring infectivity to insect cells, on the viral particle surface; method of producing thereof; and method of gene transfer using the baculovirus vector. A method of producing a baculovirus vector including; a process of cotransfecting at least a plasmid containing a gene coding a protein capable of being expressed on a cell surface and one of wild-type, mutated-type form, and recombinant baculovirus DNAs into insect cells, wherein a pseudotyped baculovirus which includes at least one part of the baculovirus DNA and is coated with the protein capable of being expressed on a cell surface, is generated.

8 Claims, 17 Drawing Sheets

Previously reported pseudotyped virus

FIG. 6

Polyhedrin promoter

GFP gene

CAG promoter

Transgene

+

IE promoter or actin promoter

Protein gene to be coated on particle

⇩ transient expression

Novel pseudotyped baculovirus

BACULOVIRUS VECTOR, METHOD OF PRODUCING THEREOF AND METHOD OF GENE TRANSFER

CROSS-REFERENCE TO RELATED APPLICATIONS

This is a continuation of Application PCT/JP2003/012275, filed on Sep. 25, 2003.

BACKGROUND OF THE INVENTION

1. Field of the Invention

The present invention relates to a baculovirus vector which is suitable for use in gene therapy, etc., a method of constructing the baculovirus vector and a method of gene transfer using the baculovirus vector.

2. Description of the Related Art

Ten years have passed since clinical studies of gene therapy started. Until now, a satisfactory outcome has not been achieved; however, this therapy, without doubt, will be at the center of advanced medical treatment in this century. Whether or not gene therapy will successfully advance depends on the development of gene transfer vectors which enable introduction of genes into target cells safely and efficiently and which have a large integration capacity.

Retroviruses, adenoviruses, adeno-associated viruses, etc. have been the main vectors used in gene therapy. However, there have been safety problems, such as the emergence of self-propagating virus and the activation of cancer genes due to random integration of genetic material, and satisfactory gene transfer efficiency and improvement of specific gene transfer methods has not been achieved. Further, there have been problems such as cytotoxicity, induction of undesirable immune reaction, and inactivation due to neutralizing antibodies.

Baculovirus, an insect virus, was thought to infect only insects until recently and had been utilized as a large-scale expression system of transgenes in insect cells.

Figure 1:
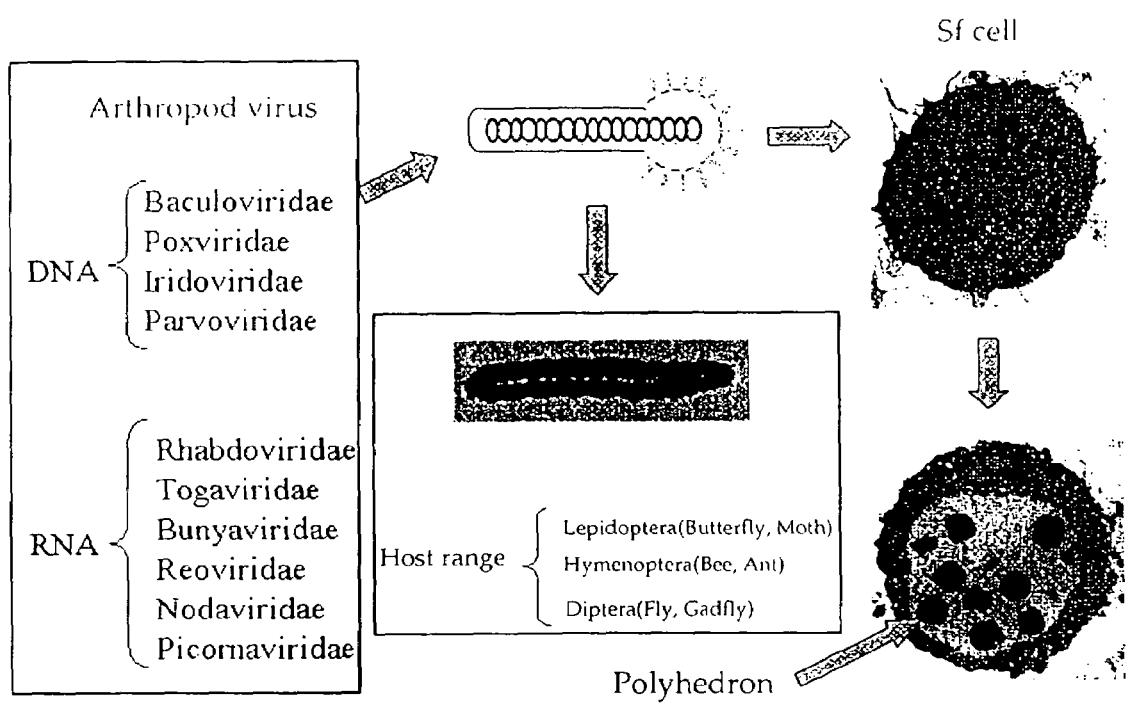
Figure 2:
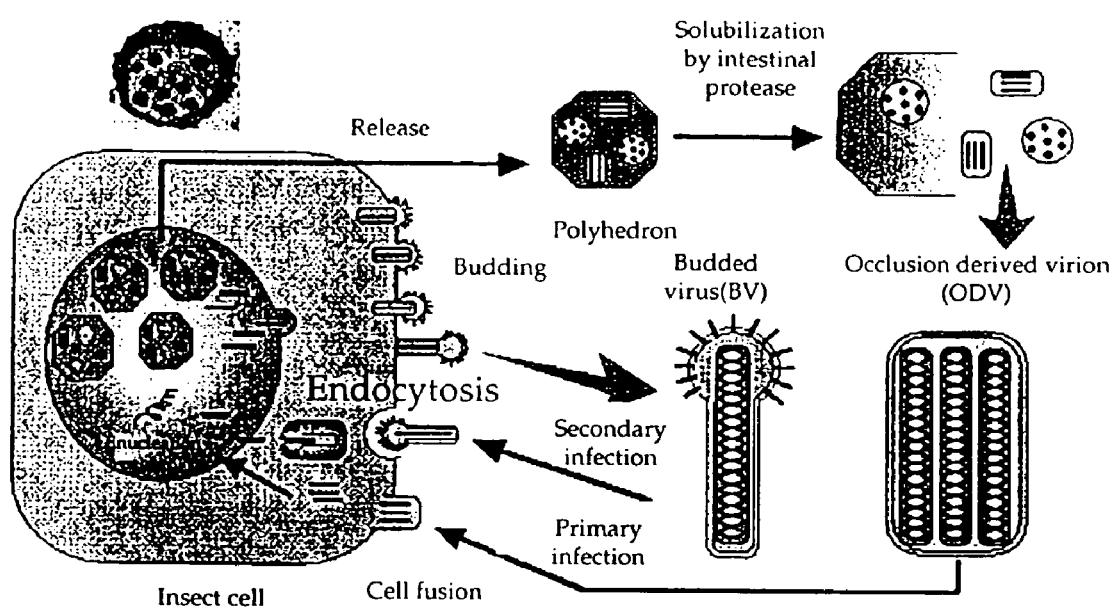

Baculoviruses are entomopathogenic viruses which infect insects such as lepidopteran, hymenopteran and diptera and have circular double-stranded DNA. Of the viruses, a group of viruses called Nuclear Polyhedorosis Virus (NPV) produce a large amount of inclusion bodies called polyhedrins in the nucleus of the infected cell during the late phase of infection. The amount of the inclusion body reaches as much as 40 to 50% of the total cell protein and the inclusion body includes a large number of viral particles (FIG. 1). Thus, even if the host is killed by infection, viruses in this polyhedrin inclusion body are protected from inactivation by, for example, ultraviolet radiation and heat, thus enabling the viruses to remain infectious for a long time (FIG. 2).

Thus, polyhedrins are essential for viruses to survive in nature, but they are not required for propagation of viruses in vitro. Therefore, if a foreign gene intended to be expressed is introduced in place of a polyhedrin gene, infection and propagation of the virus will occur and a large amount of foreign gene products will be produced without any difficulties. Until now, two viruses, Autographa californica NPV (AcNPV) and Bombyx mori NPV (BmNPV) of silkworm, have been used as vectors, but in most cases, expression is carried out using AcNPV.

The present inventors have previously succeeded in the development of the vector pAcYM1 which has the highest expression efficiency in the world among baculovirus vectors (e.g. Matsuura, Y., Possee, R. D., Overton, H. A., and Bishop, D. H. L. (1987), "Baculovirus expression vectors: the requirements for high level expression of proteins, including glycoproteins," J. Gen. Virol. 68, 1233-1250). They developed the expression of hepatitis C virus structural protein using the vector and succeeded in the development of an early stage antibody diagnosis system using it as an antigen. Due to the introduction of this diagnostic system, the incidence of post-tranfusion hepatitis C is almost conquered in Japan.

In recent years, gene transfer into mammalian cells using baculovirus has been reported (e.g. Hofmann, C., Sandig, V., Jennings, G., Rudolph, M., Schlag, P., and Strauss, M. (1995), "Efficient gene transfer into human hepatocytes by baculovirus vectors," Proc. Natl. Acad. Sci. USA 92, 10099-10103, and Boyce, F. M., and Bucher, N. L. R. (1996), "Baculovirus-mediated gene transfer into mammalian cells," Proc. Natl. Acad. Sci. USA 93, 2348-2352). At first, it was thought gene transfer using baculovirus was specific to hepatocytes; however, the present inventors demonstrated the capability of gene transfer into a wide variety of animal cells (e.g. Shoji I., Aizaki H., Tani H., Ishii K., Chiba T., Saito I., Miyamura T., and Matsuura Y. (1997), "Efficient gene transfer into various mammalian cells including non-hepatic cells by baculovirus vectors," J. Gen. Virol. 78, 2657-2664).

In this way, it has been demonstrated that baculovirus vectors infect a wide variety of mammalian cells and can express foreign genes efficiently without replication. Therefore, the baculovirus vectors have attracted attention as a potential gene therapy vector.

Baculovirus vectors have extraordinary properties as a gene transfer vector into humans for the following reasons: 1) the virus gene is as large as 130 kbp, which allows insertion of large (<15 kbp) foreign genes, 2) since the virus gene is not expressed in mammalian cells, it hardly causes cytotoxicity and a harmful immune response is not induced, 3) recombinant virus can be prepared in a short time, 4) there exists no neutralizing antibody against baculovirus in the human, etc.

Figure 3:
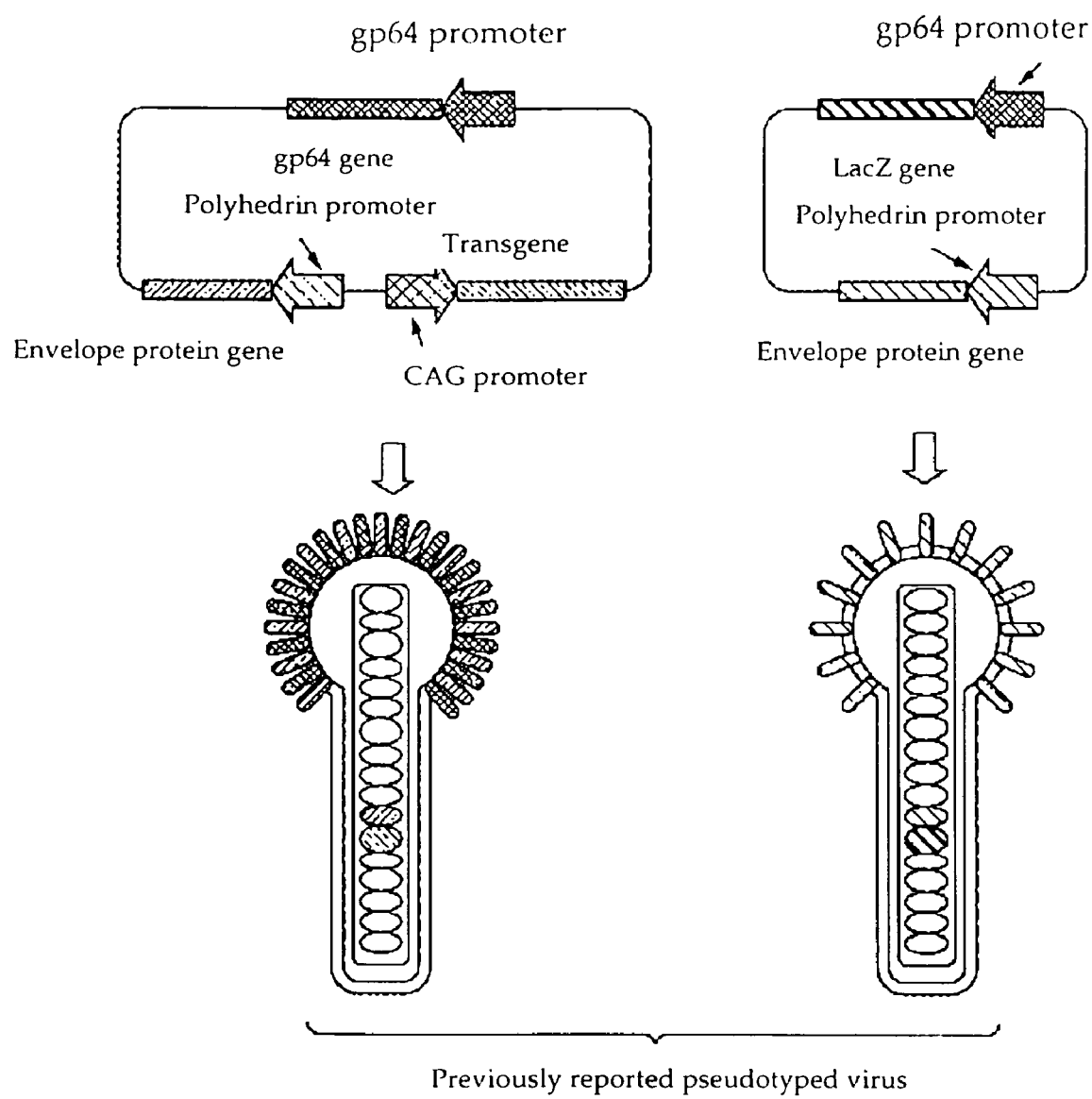

In order to improve the infection efficiency in mammalian cells, an attempt has been made to provide other virus envelope proteins such as vesicular stomatitis virus G protein in baculovirus (e.g. Tani, H., Nishijima, M., Ushijima, H., Miyamura, T., and Matsuura, Y. (2001), "Characterization of cell-surface determinants important for baculovirus infection," Virology 279, 343-353) (FIG. 3 left). This remarkably improved the gene transfer efficiency into mammalian cells.

Further, another attempt has been made to completely replace the baculovirus gp64 protein with the envelope protein of another virus, and it is reported that the recombinant virus can replicate in insect cells when the gp64 protein is replaced by envelope proteins of closely related virus or vesicular stomatitis virus G protein, (e.g. Mangor J. T., Monsam S. A., Johnson C. M., and Blissard G. W. (2001), "A gp64-null baculovirus pseudotyped with vesicular stomatitis virus G protein." J. Virol. 75, 2544-2556).

However, in these conventional methods, viruses are required to be infectious to insect cells to obtain a high titer of stock virus. Thus in these prior methods, proteins having no infectivity to insect cells could not be selected.

Therefore, it is impossible to make infection of these vectors specific and a baculovirus vector capable of conferring specificity has not been reported. The development of a baculovirus vector which has the above-mentioned excellent properties and which is capable of conferring the desired infectiousness was strongly desired.

SUMMARY OF THE INVENTION

An object of the present invention is to solve the above-mentioned problems and to achieve the following goals. Specifically, an object of the present invention is to provide a novel baculovirus vector which can provide a desired protein on the viral particle surface and which does not require infectiousness to insect cells; a method of producing thereof; and a method of gene transfer using the baculovirus vector.

The inventors have achieved the present invention based on the development of methods in which the gp64 gene of a baculovirus is removed and instead the virus is allowed to uptake a gene encoding a protein of interest.

Specifically, the means for solving the above-mentioned problems are as follows

<1> A method of producing a baculovirus vector comprising cotransfecting insect cells with at least one plasmid containing a gene encoding a protein which is capable of being expressed on a cell surface and either a wild-type, mutant, or recombinant baculovirus DNA, thereby generating a pseudotyped baculovirus which comprises at least one part of the baculovirus DNA and whose cell surface is coated with the protein capable of being expressed.

<2> A method of producing a baculovirus vector according to <1>, wherein the baculovirus DNA is a recombinant baculovirus DNA and wherein, in the baculovirus DNA, a polyhedrin gene and a first foreign gene have been homologously recombined and a gp64 gene and a second foreign gene have been homologously recombined.

<3> A method of producing a baculovirus vector according to <1>, wherein the baculovirus DNA is a recombinant baculovirus DNA and wherein, in the baculovirus DNA, a polyhedrin gene and a first foreign gene have been homologously recombined.

<4> A method of producing a baculovirus vector according to <3>, wherein, in the process of cotransfecting, a vector containing a second foreign gene is cotransfected at the same time, wherein a homologous recombination between a gp64 gene and the second foreign gene occurs, thereby generating a pseudotyped baculovirus which comprises the baculovirus DNA containing foreign genes and whose cell surface is coated with the protein capable of being expressed on a cell surface.

<5> A method of producing a baculovirus vector according to any one of <2> to <4>, wherein the first foreign gene is either a transgene or a marker gene.

<6> A method of producing a baculovirus vector according to any one of <2> to <4>, wherein the second foreign gene is either a transgene or a marker gene.

<7> A method of producing a baculovirus vector according to any one of <1> to <6>, where the protein capable of being expressed on a cell surface is a protein that cannot infect insect cells.

<8> A method of producing a baculovirus vector according to any one of <1> to <6>, where the protein capable of being expressed on a cell surface is a protein which can infect insect cells.

<9> A method of producing a baculovirus vector according to <8>, further comprising after the cotransfecting step, a process of amplifying which comprises: infecting cells in which the plasmid containing a gene coding a protein capable of being expressed on a cell surface is expressed with a first pseudotyped baculovirus generated by the process of cotransfecting, and amplifying the virus to thereby generate a second pseudotyped baculovirus.

<10> A method of producing a baculovirus vector according to <1>, wherein the baculovirus DNA is a recombinant baculovirus DNA which lacks the gp64 gene, and wherein, in the process of cotransfecting, a vector containing a transgene is further cotransfected.

<11> A method of producing a baculovirus vector comprising infecting insect cells with a baculovirus which lacks the gp64 gene which coats a particle surface with gp64 protein, where a protein capable of being expressed on a cell surface is transiently expressed on its surface, and allowing a viral particle coated with the protein capable of being expressed on a cell surface to bud from the cell surface.

<12> A baculovirus vector, which is produced by the method of producing a baculovirus vector of any one of <1> to <11>.

<13> A baculovirus vector, comprising: a baculovirus DNA which lacks the gp64 gene, wherein the baculovirus is a pseudotyped virus coated with a protein which is incapable of infecting insect cells.

<14> A baculovirus vector, comprising: a baculovirus DNA which lacks the gp64 gene, wherein the baculovirus is a pseudotyped virus coated with a protein which capable of infecting insect cells, and wherein the protein is not a protein expressed from the baculovirus DNA.

<15> A baculovirus vector according to <12> to <14>, which is capable of specific gene transfer by selecting cells.

<16> A method of gene transfer comprising: transferring a gene into a cell either in vivo or in vitro using the baculovirus vector of any one of <12> to <15>.

BRIEF DESCRIPTION OF THE DRAWINGS

FIG. 1 is a diagram explaining an infection of insect cells by baculovirus polyhedrin.

FIG. 2 is a diagram illustrating a life cycle of a baculovirus.

FIG. 3 is a diagram illustrating a conventional recombinant vector.

FIG. 4 is a diagram illustrating a conventional recombinant vector.

FIG. 5 is a diagram illustrating the preparation of a novel pseudotyped baculovirus.

FIG. 6 is a diagram illustrating the preparation of a novel pseudotyped baculovirus.

FIG. 7 is a diagram illustrating the preparation of a novel pseudotyped baculovirus.

FIG. 8 is a diagram illustrating the preparation of a gp64 knockout vector.

FIG. 9 is a diagram illustrating the preparation of a gp64 defective baculovirus AcΔ64/GFP/LacZ.

FIG. 10 is a diagram illustrating the preparation of a plasmid capable of transiently expressing gp64 protein in insect cells.

FIG. 11 is a diagram illustrating an example of the preparation of a gp64 gene defective virus AcΔ64/GFP/LacZ*64 transiently coated with the gp64 protein.

FIG. 12 is a diagram illustrating the amplification of AcΔ64/GFP/LacZ*64.

FIG. 13 is a diagram illustrating the preparation of AcΔ64/GFP/LacZ*64 having a luciferase gene and transiently coated with the gp64 protein.

FIG. 14 is a diagram illustrating the preparation of a pseudotyped virus coated with the G protein of vesicular stomatitis virus.

FIG. 15 is a diagram illustrating the characteristics of a pseudotyped virus coated with the G protein of vesicular stomatitis virus.

FIG. 16 is a diagram illustrating gene transfer by a pseudotyped virus coated with the G protein of vesicular stomatitis virus.

FIGS. 17A and 17B are diagrams illustrating the results of a neutralization test of a pseudotyped virus coated with the G protein of vesicular stomatitis virus.

DESCRIPTION OF THE PREFERRED EMBODIMENTS

Outline of Construction of a Targeting Vector

Figure 4:
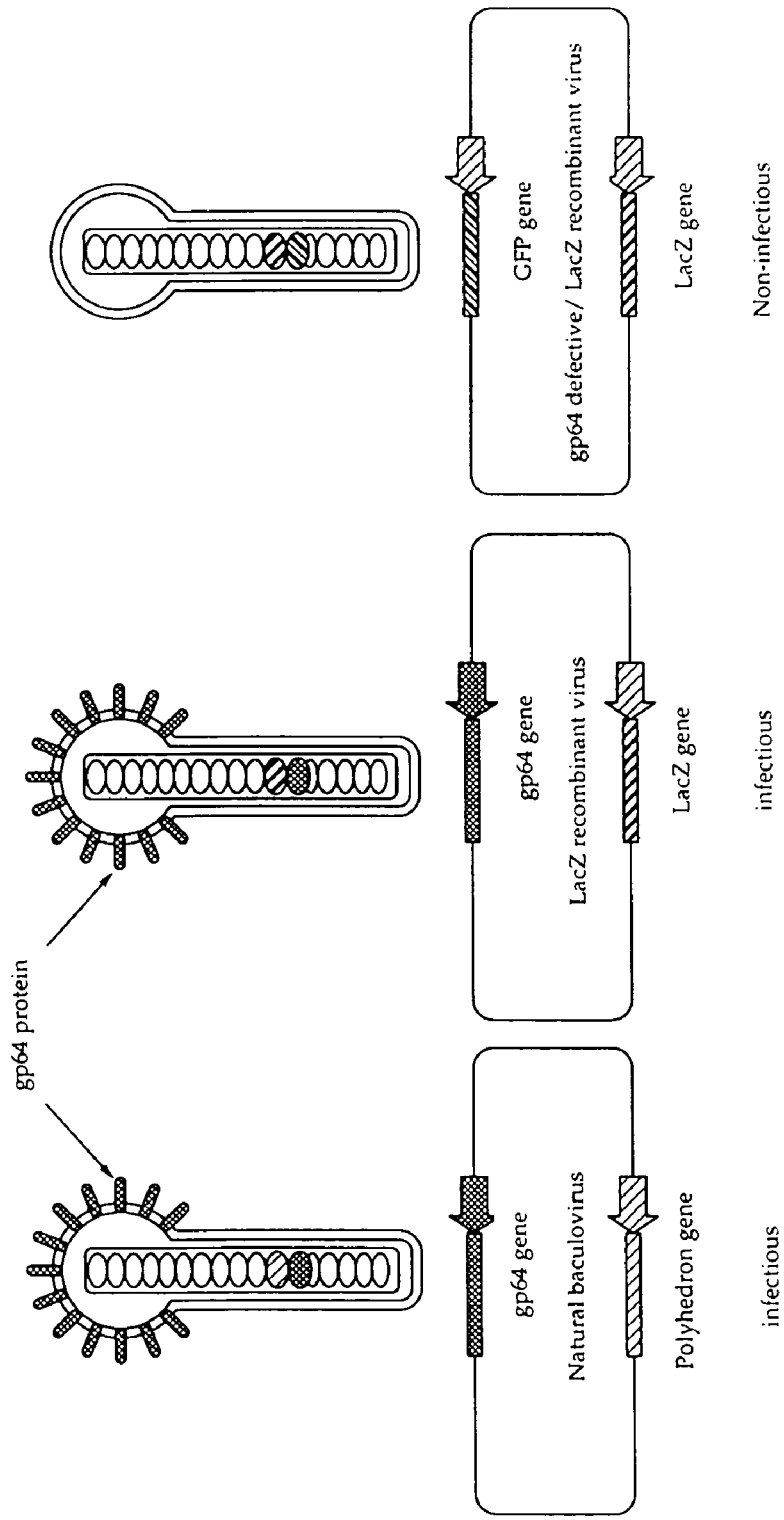

The present inventors have revealed that recognition of phosphatidylinositol (PI) on the cell surface by the gp64 protein of the baculoviral particle is important for the baculovirus to invade mammalian cells (Tani et al., 2001). Since PI is found in a variety of cells, it is impossible to confer cell specificity to a baculovirus vector as long as it retains gp64 (FIG. 4).

Further, as mentioned above, according to the method of recombining envelope protein, it is essential for the envelope protein to retain its infectiousness to insect cells, and thus the kinds of envelope proteins are restricted to proteins having universal infectiousness to cells.

Figure 5:
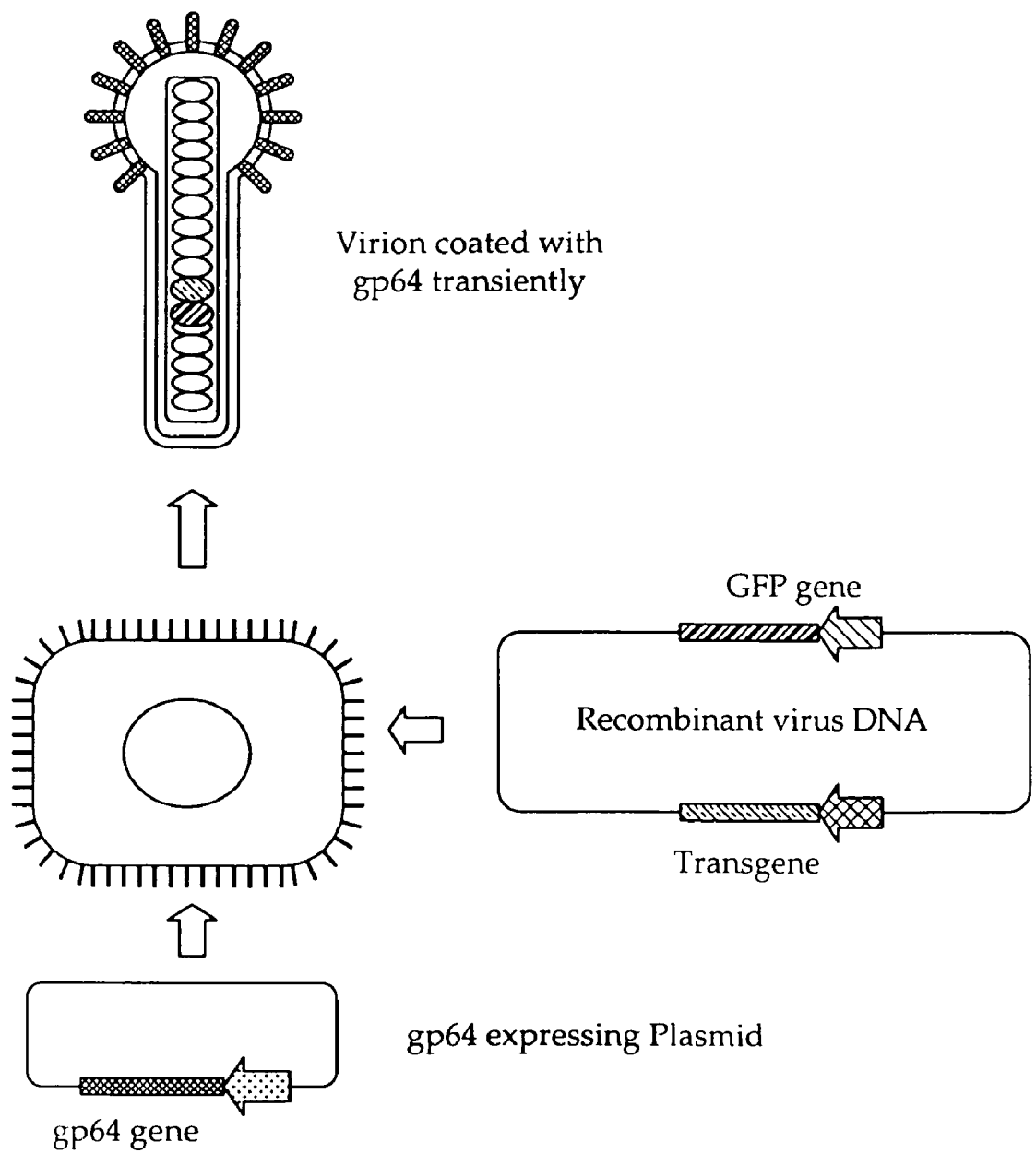

If the development of a targeting vector is desired, it is necessary to prepare a recombinant virus which completely lacks the gp64 protein and which has only the ligand molecule of interest. First, insect cells which transiently express gp64 protein are transfected with gp64 gene defective virus DNA to thereby construct a system from which viruses having a particle surface transiently coated with gp64 protein can be collected (FIG. 5).

Figure 7:
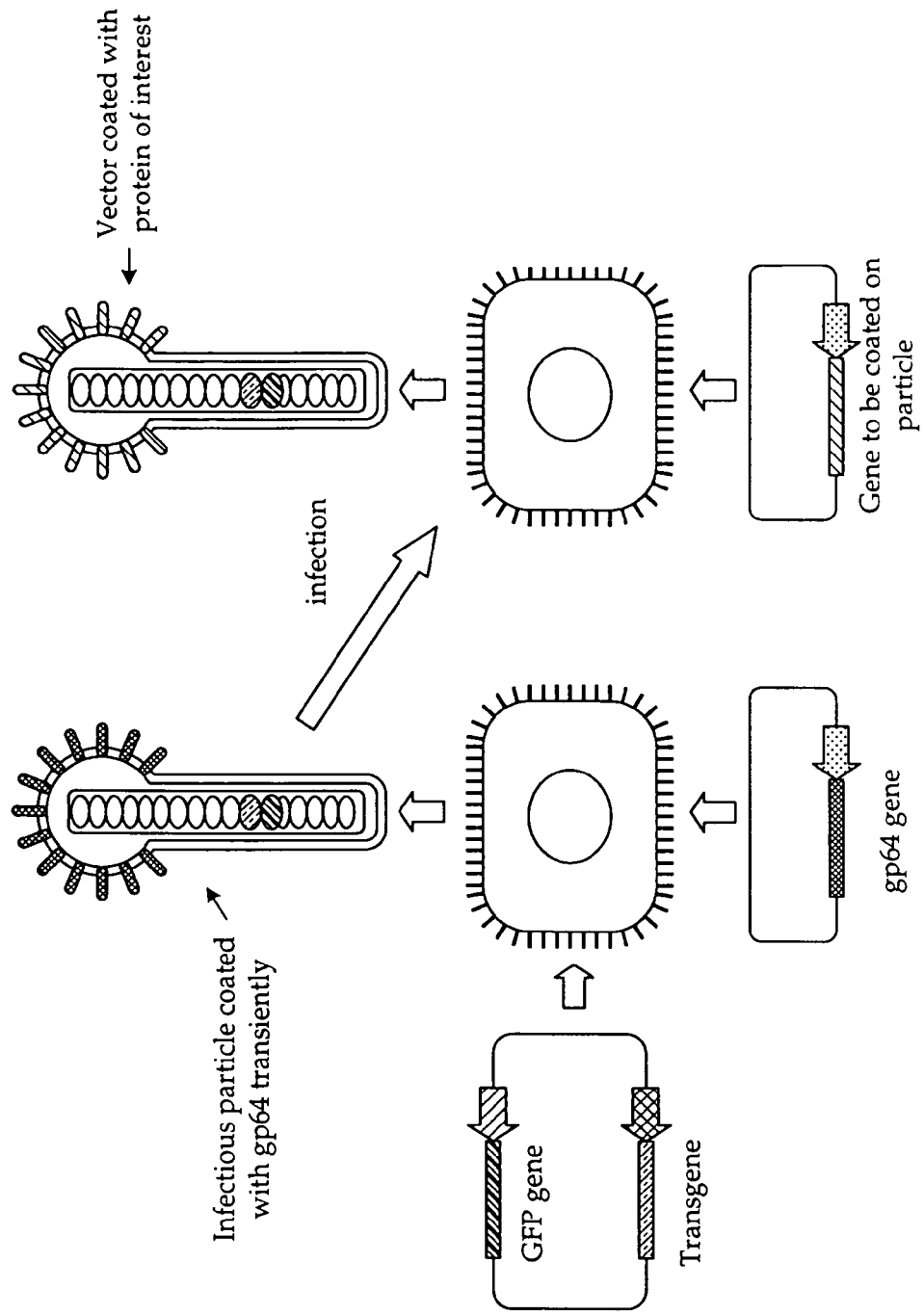

These recombinant viruses can infect insect cells via the gp64 protein only once. Thus, when this virus is allowed to infect insect cells which already express the ligand molecules of interest on the surface of the cell, viral particles coated with the ligand molecule of interest will bud from the cell surface (FIGS. 6 and 7). It was considered that allowing the virus to be transiently coated with a protein by expressing an envelope protein using a plasmid would be difficult from the viewpoint of gene transfer efficiency.

The method of producing a baculovirus vector comprises a process of cotransfecting insect cells with at least a plasmid containing a gene coding a protein capable of being expressed on a cell surface and either a wild-type, mutant or recombinant baculovirus DNA, wherein a pseudotyped baculovirus is generated which comprises at least one part of the baculovirus DNA and which is coated with the protein capable of being expressed on a cell surface.

In the present invention, a pseudotyped baculovirus means a baculovirus which has a protein on its surface which is not derived from the virus DNA thereof. Specifically, it refers to a virus coated with a protein which was transiently expressed by a separately introduced plasmid. This definition of pseudotyped baculovirus includes a baculovirus coated with gp64 (a baculovirus envelope protein) when the gp64 protein is not derived from the virus DNA but instead from a plasmid, for example, because the virus DNA gp64 region of the baculovirus is defective. Here, "transiently expressed" refers to expression without being integrated into virus DNA.

The protein capable of being expressed on a cell surface may be a protein which cannot infect insect cells or a protein which can infect insect cells. Here, a protein which can infect insect cells means a protein which enables virus entry into insect cells when it is expressed on a baculovirus envelope. When a vector is used for human transfection, etc. infectiousness to insect cells is not required; however, when a vector is used as an intermediate for preparation of a final vector, the vector must be able to infect insect cells to propagate.

Examples of the protein which can infect insect cells include the gp64 protein, envelope proteins of viruses closely related to baculovirus, and the G protein of vesicular stomatitis virus.

The protein which cannot infect insect cells is not particularly limited as long as it is a protein which can be expressed on a cell surface. It is preferably a ligand or receptor corresponding to receptor and antigen which are specific to the cell or tissue in vivo into which genes are expected to be transferred. Examples include molecules which can recognize a cancer specific antigen, cell surface molecules different from normal cells, and receptor molecules against antigens expressed specifically in cells infected by viruses such as the AIDS virus.

Herein, the insect cells to be transfected are not particularly limited, but Sf9 cells can be suitably used.

The plasmid containing a gene coding a protein capable of being expressed on a cell surface can be prepared by suitably selecting a plasmid from known plasmids and inserting a gene coding a desired protein. Examples of suitable plasmids include pIB/gp64 and pA3Fb/gp64, which are described in the Examples below.

Moreover, the promoter in the plasmid is a promoter other than a gp64 promoter, is preferably a promoter which expresses in insect cells and is particularly preferably an actin promoter.

The baculovirus DNA may be a wild-type, mutant or recombinant baculovirus DNA, but it is preferred that the baculovirus DNA is a recombinant baculovirus DNA where a homologous recombination between the polyhedrin gene and a first foreign gene has been performed and a homologous recombination between the gp64 gene and a second foreign gene has been performed.

Further, it is preferred that the baculovirus DNA is a recombinant baculovirus DNA where a polyhedrin gene and a first foreign gene have been homologously recombined. In this case, it is preferable that in the cotransfecting process, a vector containing the second foreign gene is cotransfected simultaneously, with homologous recombination between the gp64 gene and the second foreign gene.

The foreign gene to be homologously recombined is preferably either a transgene, which is a gene of interest introduced into target cells, or a marker gene, which is used as an index of isolation or introduction, etc. More preferably, the first foreign gene is a transgene. Furthermore, the foreign gene to be homologously recombined preferably has a promoter, for example, a polyhedrin promoter, which allows the gene to be expressed at a high level in insect cells. When a final vector adapted to a host is prepared, a promoter which expresses in the cell is used as the transgene promoter.

The promoter expressed in human is not particularly limited, but a CAG promoter composed of chicken β actin promoter and CMV enhancer, CMV promoter, RSV promoter, etc. are preferred.

Further, the foreign gene to be introduced is not particularly limited as long as it can be expressed by the above-mentioned promoter, but from the viewpoint of usefulness, defective genes related to various kinds of genetic diseases, cytokines, neurotrophic factors, nonself-antigen genes, nucleotide sequences coding virus antigens, etc., cancer suppressor genes, antisense sequences such as Ras, cancer genes, or suicide genes such as thymidine kinase, etc. are preferred.

Further, it is preferable, from a viewpoint that amplification is easily achieved, that the method of producing a baculovirus vector further comprises an amplifying process after the cotransfecting process. The amplifying process comprises infecting cells which express the plasmid containing a gene coding a protein capable of being expressed on a cell surface with a first pseudotyped baculovirus generated by the cotransfecting process, and amplifying the virus to thereby generate a second pseudotyped baculovirus.

Further, the method of producing a baculovirus vector according to another aspect of the present invention comprises a cotransfecting process in which a plasmid containing a gene coding a protein capable of being expressed on a cell surface, a recombinant baculovirus DNA which is defective in gp64 gene, and a vector containing a transgene is cotransfected into insect cells and a pseudotyped baculovirus coated with the protein capable of being expressed on a cell surface, is generated. The recombinant baculovirus DNA which is defective in gp64 gene is preferably a recombinant baculovirus DNA which has two kinds of genes containing a polyhedrin promoter and a marker downstream thereof.

Further, the method of producing a baculovirus vector according to another aspect of the present invention comprises at least a budding process which comprises infecting insect cells expressing a protein capable of being transiently expressed on a cell surface on its surface with a gp64 gene defective baculovirus having a particle surface coated with gp64 protein, and allowing a viral particle coated with the protein capable of being expressed on a cell surface to bud from the cell surface.

Here, insect cells expressing a protein capable of being transiently expressed on a cell surface refers to insect cells which express a protein by a plasmid, and which can be obtained by introducing a plasmid coding the protein.

The method of producing a baculovirus vector may further comprise the step of preparing a gp64 gene defective baculovirus having a particle surface coated with the gp64 protein, before the process of allowing a baculovirus having a particle surface coated for only one generation with a gp64 protein to bud by transfecting insect cells which transiently express a protein with the gp64 gene defective virus DNA.

The baculovirus vector of the present invention is produced by the method of producing a baculovirus vector of the present invention.

Regarding other methods, such as the handling of insect cells, a general method of gene recombination and cotransfection, a similar technique as the known method of preparing a recombinant virus from insect cells (Yoshiharu Matsuura, Protein, Nucleic Acid and Enzyme, 37, 211-222, 1992, and Yoshiharu Matsuura, baculovirus expression system, "gene transfer and expression/analysis method" edited by Takashi Yokota and Kenichi Arai, Yodosya, Yoshiharu Matsuura, Cell 33 (2) 30-34, 2001).

For example, a transfer vector containing a gene to be expressed, infectious virus DNA and, in case of the present invention, a plasmid, are simultaneously introduced into Sf9 cells ($0.8 \times 10^6$/35 mm dish). The culture supernatant is diluted on the $4^{th}$ day to allow plaque formation. The plaques were suspended in 400 µl of culture medium, viruses are eluted from agar by vortexing and centrifuged to harvest the supernatant. This supernatant is inoculated into Sf9 cells, etc., which transiently expressed envelope protein, and after cultivation, supernatant is collected once again to obtain white virus pellets. The plasmid is preferably introduced into Sf9 cells ($1 \times 10^6$/35 mm) using 2 µg of plasmid DNA and about 6 µl of transfection reagent (manufactured by UniFactor, Bridge, etc.).

Moreover, the baculovirus is infectious to mammalian cells and introduces a gene into the nucleus, but it does not propagate in the cells. Therefore, in order to obtain high expression, it is required to prepare a virus having a high infectious titer ($1 \times 10^9$-10 pfu/ml by purification and introduce highly copied genes. In the method of producing a baculovirus of the present invention, this can be achieved by infecting cells which transiently express the plasmid having the desired protein with a gp64 gene defective baculovirus having a particle surface coated with gp64 protein, and carried out, for example, using the following known method except for making the plasmid expressed.

0.5 ml to 1.0 ml of stock virus (normally $1 \times 10^{7-8}$ pfu/ml) is inoculated into Sf9 cells ($1.0 \times 10^7$/10 cm dish), after 4 days of infection, culture supernatant is collected, lightly centrifuged (6,000 g, 10 minutes) to thereby remove cell debris and stored. This surpernatant is centrifuged at 25,000 rpm in an SW28 rotor (Beckman) for 60 minutes at 4° C. and the obtained virus pellet is suspended in 1 ml of PBS. This is loaded on 10 to 60% of sucrose gradients and is centrifuged at 25,000 rpm in an SW41 rotor (Beckman) for 60 minutes at 4° C. The virus band is collected. After suspension in PBS, the virus is centrifuged at 25,000 rpm in an SW41 rotor for 60 minutes at 4° C. The purified virus pellet is suspended in 1 ml of PBS and stored at 4° C. away from light. The infectious titer of the purified virus can be measured by a plaque assay using Sf9 cells. Normally, $0.2 \times 10^{10}$ pfu/ml of purified virus is obtained from 250 to 500 ml of culture supernatant.

Moreover, the baculovirus vector according to another aspect of the present invention comprises a baculovirus DNA which is defective in the gp64 gene, wherein the baculovirus is a pseudotyped virus coated with a protein incapable of infecting insect cells. Examples thereof include baculovirus vector which comprises a baculovirus DNA in which a marker gene with a polyhedrin promoter is introduced into the gp64 gene region containing a gp64 promoter region and polyhedrin gene region, respectively, and which baculovirus vector is coated with any plasmid-derived protein capable of being expressed transiently on a cell surface and incapable of infecting insect cells, but the derivation of the protein incapable of infecting insect cells is not limited to these examples.

Moreover, another baculovirus vector of the present invention is a baculovirus vector comprising a baculovirus DNA which is defective in gp64 gene, wherein the baculovirus is a pseudotyped virus coated with a protein capable of infecting insect cells, and wherein the protein is not a protein expressed from the baculovirus DNA. The baculovirus vector may be a vector which does not contain a transgene and which is transiently coated with a gp64 protein such as AcΔ64/GFP/LaCZ*64 (FIGS. 11 and 12) mentioned later, a vector with a transgene integrated and the vector being transiently coated with a gp64 protein such as AcΔ64/GFP/CAGluc*64 (FIG. 13), and a vector with transgene integrated and the vector being transiently coated with a protein other than gp64 protein and which is capable of being expressed on a cell surface and capable of infecting insect cells.

The pseudotyped baculovirus vector coated with a protein capable of infecting insect cells can be used for propagation of the baculovirus vector in insect cells and can be used as a stock.

The pseudotyped baculovirus vector coated with a protein incapable of infecting insect cells can be used as a final vector for introducing genes either into cells in vivo (including human cells) or in vitro. When the baculovirus vector is administered into a living organism, it can be administered orally or non-orally (e.g. injection into vein, muscle, peritoneal cavity, and under or into the skin, intrarectal administration, transmucosal administration, administration into an organ, etc.). The amount and number of doses can be suitably controlled according on the weight of the subject and the gene to be transferred.

In some cases, gene expression in vivo is interfered by complement inactivation, but the inactivation can be circumvented by simultaneously applying nafamstat mesilate, which is a proteolysis inhibitor of the complement.

The method of gene transfer of the present invention comprises transferring a gene into cells, either in vivo or in vitro, using the baculovirus vector of the present invention.

Gene transfer into mammalian cells can be carried out in the same way as for normal virus vectors. For example, mammalian cells into which the gene is to be transferred are prepared in a plate or dish with 60 to 80% of mammalian cells confluent. The method of infection is the same as that in normal virus inoculation. First, culture supernatant is removed, the recombinant virus is inoculated at a multiplicity of infection (moi) of 10 to 100 and incubated for 30 to 60 minutes. Then, medium is added and cultured at 37° C. At 24 to 48 hours postinfection, cells are collected and gene expression is examined. Further, since the baculovirus may be inactivated by a complement in serum, it is preferred that the fetal bovine serum in culture medium is inactivated.

EXAMPLES

The baculovirus vector and method of producing thereof, and method of transferring gene using the baculovirus vector of the present invention will be illustrated in further detail with reference to several examples below, which are not intended to limit the scope of the present invention.

Example 1

Preparation of a gp64 Knockout Vector

Figure 8:
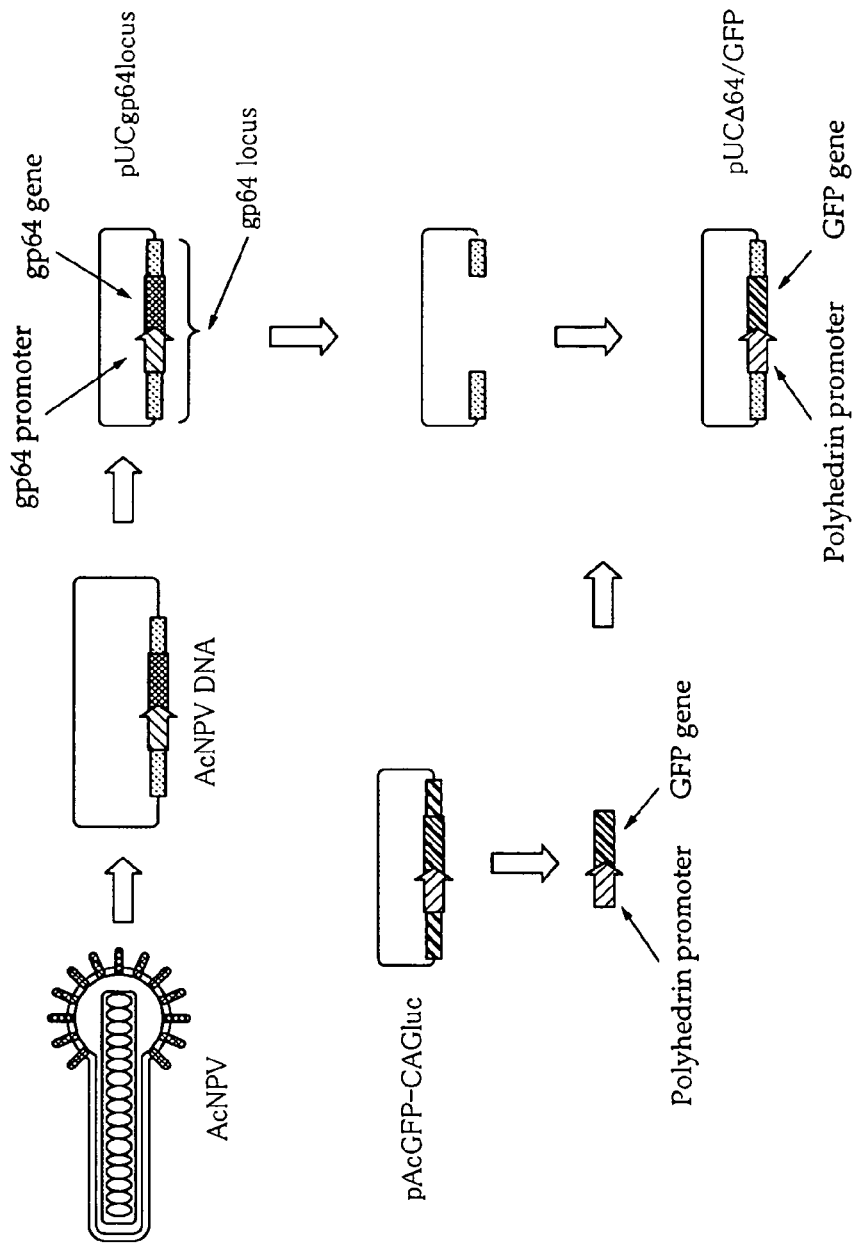

In order to eliminate the expression of gp64 by replacing the gp64 gene region of baculovirus with a polyhedrin promoter and green fluorescent protein (GFP) gene, knockout vector pUCΔ64/GFP was prepared according to the procedure shown in FIG. 8.

An EcoRI-SmaI fragment (nt 107,325-112,049) containing the gp64 gene region of AcNPV was inserted into the same restriction enzyme site of pUC18 to create pUCgp64locus. Next, transfer vector pAcGFP-CAGluc (Tani et al., 2001) where GFP gene and luciferase gene were inserted downstream of the polyhedrin promoter and downstream of the CAG promoter (Niwa et al., 1986) developed by Miyazaki et al., respectively, was cleaved at EcoRV and SnaBI and the fragment containing the polyhedrin promoter and GFP gene was collected. The fragment was inserted into the site blunted by the klenow fragment after cleavage of pUCgp64locus at SpeI (nt 109,761) and BglII (nt 108,039) to thereby prepare gp64 gene knockout vector, pUCΔ64/GFP.

Example 2

Figure 9:
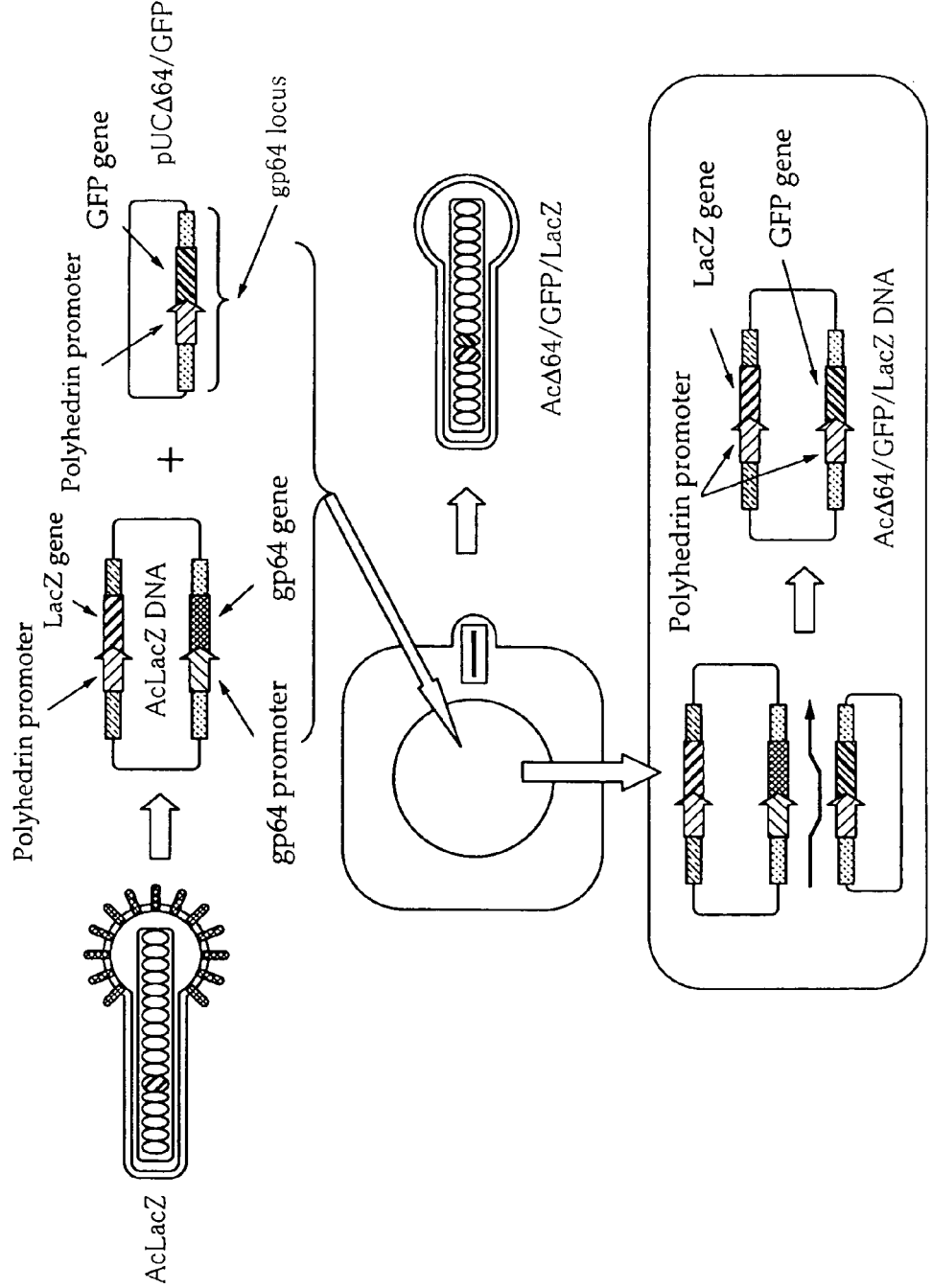

Preparation of gp64 Gene Defective Baculovirus AcΔ64/GFP/LacZ (FIG. 9)

An infectious virus DNA was extracted from recombinant baculovirus (AcLacZ) in which the beta galactosidase (LacZ) gene had been inserted downstream of the polyhedrin promoter, and Sf9 cells were cotransfected together with the gp64 gene knockout vector, pUCΔ64/GFP. In the insect cells' nucleus, homologous recombination between virus DNA and pUCΔ64/GFP occurred, thus resulting in recombinant virus AcΔ64/GFP/LacZ where the gp64 gene region of the baculovirus DNA was replaced by the polyhedrin promoter and the GFP gene. This virus is defective in gp64 gene and its promoter region and because the virus is completely defective in envelope protein, it is not infectious. Thus, AcΔ64/GFP/LacZ must be modified by transiently coating the AcΔ64/GFP/LacZ with gp64 protein so that it can infect only once.

Example 3

Figure 10:
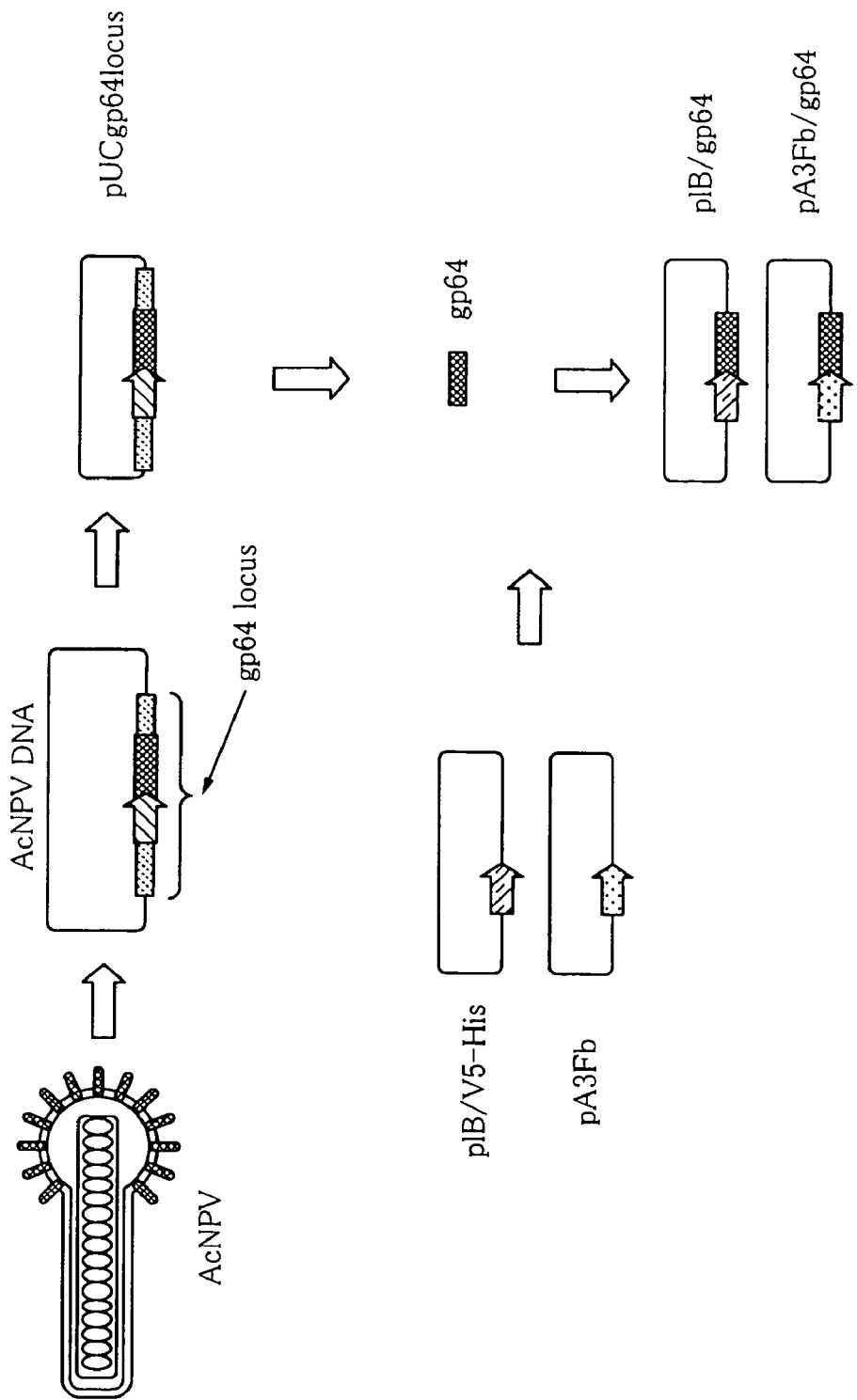

Preparation of a Plasmid which is Capable of Transiently Expressing gp64 Protein in Insect Cells (FIG. 10)

In order to prepare a plasmid capable of expressing gp64 protein in Sf9 cells, a SpeI-BglII fragment containing the gp64 gene was cut out from pUCgp64locus and the fragment was inserted into the pUC18 which was cleaved with the same restriction enzyme to prepare pUCgp64. Moreover, a Hind III-EcoRI fragment containing the gp64 gene was cut out from pUCgp64 and the fragment was inserted into the pIB/V5-His (Invitrogen) which was cleaved with the same restriction enzyme to prepare expression vector pIB/gp64. Genes inserted downstream of the baculovirus early gene promoter (IE promoter) of pIB/V5-His can be expressed efficiently in insect cells. Moreover, a similar expression vector was prepared utilizing an actin promoter which is transcribed at a high rate in insect cells. First, gp64 gene was amplified by PCR using pUCgp64locus as a template. As a primer, gp64-Fw (Bgl): AAAGATCTACCatggtaagcgctattgttt (SEQ ID No 1) and gp64-Rv (Sal): TTGTCGACttaatattgtctattacggttt (SEQ ID NO 2) were used. The amplified gp64 gene was cleaved with BglII and SalI and inserted into the BglII-SalI site of pA3Fb to prepare a pA3Fb/gp64.

Example 4

Figure 11:
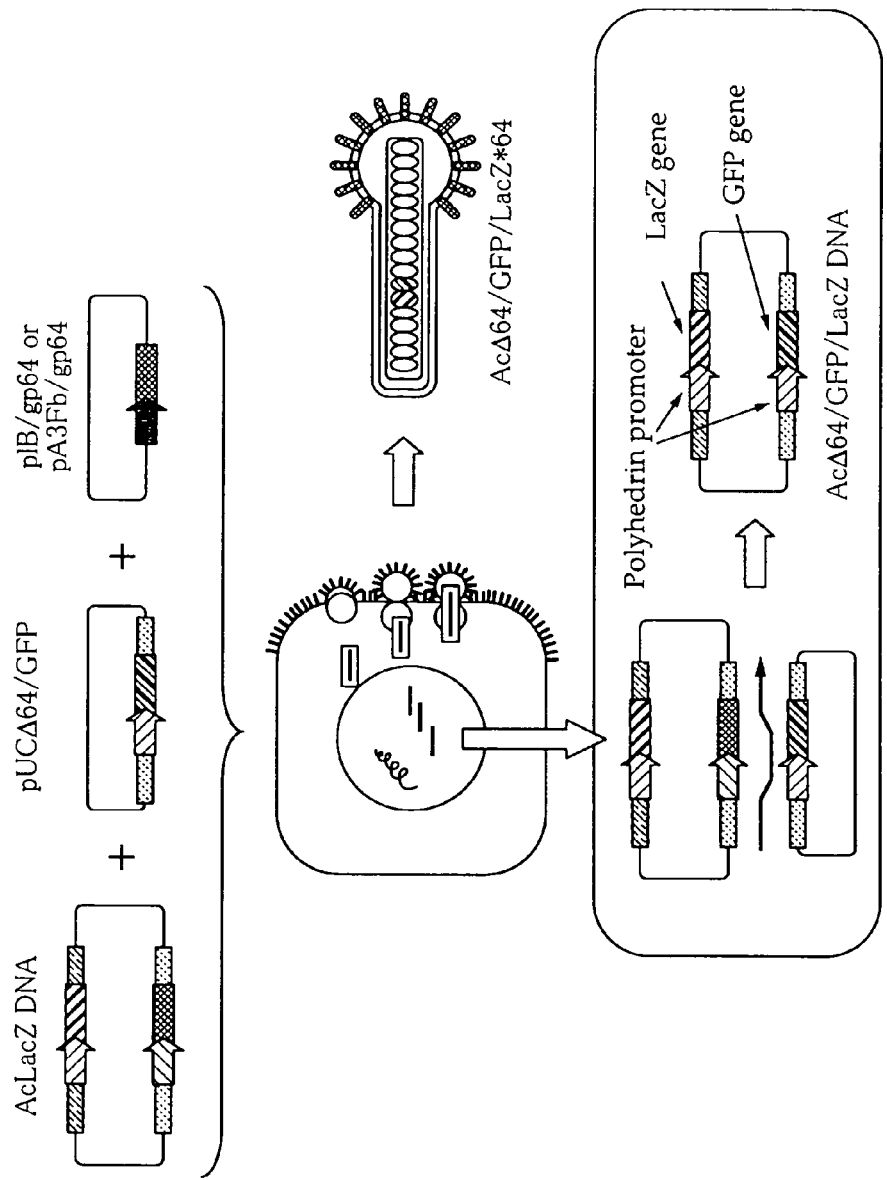

Preparation of the gp64 Gene Defective Virus AcΔ64/GFP/LacZ*64 Transiently Coated with gp64 Protein (FIG. 11)

Sf9 cells were cotransfected with the above-mentioned infectious virus DNA of AcLacZ, pUCΔ64/GFP, and pIB/gp64 or pA3Fb/gp64. This causes a homologous recombination between virus DNA and pUCΔ64/GFP in the nucleus of the insect cells, thus resulting in the recombinant virus AcΔ64/GFP/LacZ, whose gp64 gene region of baculovirus DNA has been replaced by the polyhedrin promoter and the GFP gene. Since this virus is defective in the gp64 gene and its promoter region, the virus cannot propagate in normal insect cells. However, a gp64 protein has been supplied to the surface of the cells by cotransfection with pIB/gp64 or pA3Fb/gp64, and thus, the virus is coated with gp64 protein, retains its infectiousness in spite of the lack of the gp64 gene, and can bud. In addition, the recombinant virus can be distinguished from the parent AcLacZ using the expression of GFP as a marker. Specifically, the recombinant virus expresses both LacZ and GFP. Practically the virus was separated as follows. Specifically, from the culture supernatant on the 4th day after transfection, both GFP- and LacZ-positive plaques where homologous recombination was considered to occur were collected by normal plaque assay using Sf9 cells cotransfected with pIB/gp64 or pA3Fb/gp64 the day before. Plaque assays were repeated four times to be purified, and thus, obtained AcΔ64/GFP/LacZ*64 where gp64 gene region was replaced by a polyhedrin promoter and GFP gene and transiently coated with a gp64 protein to retain infectiousness.

Example 5

Figure 12:
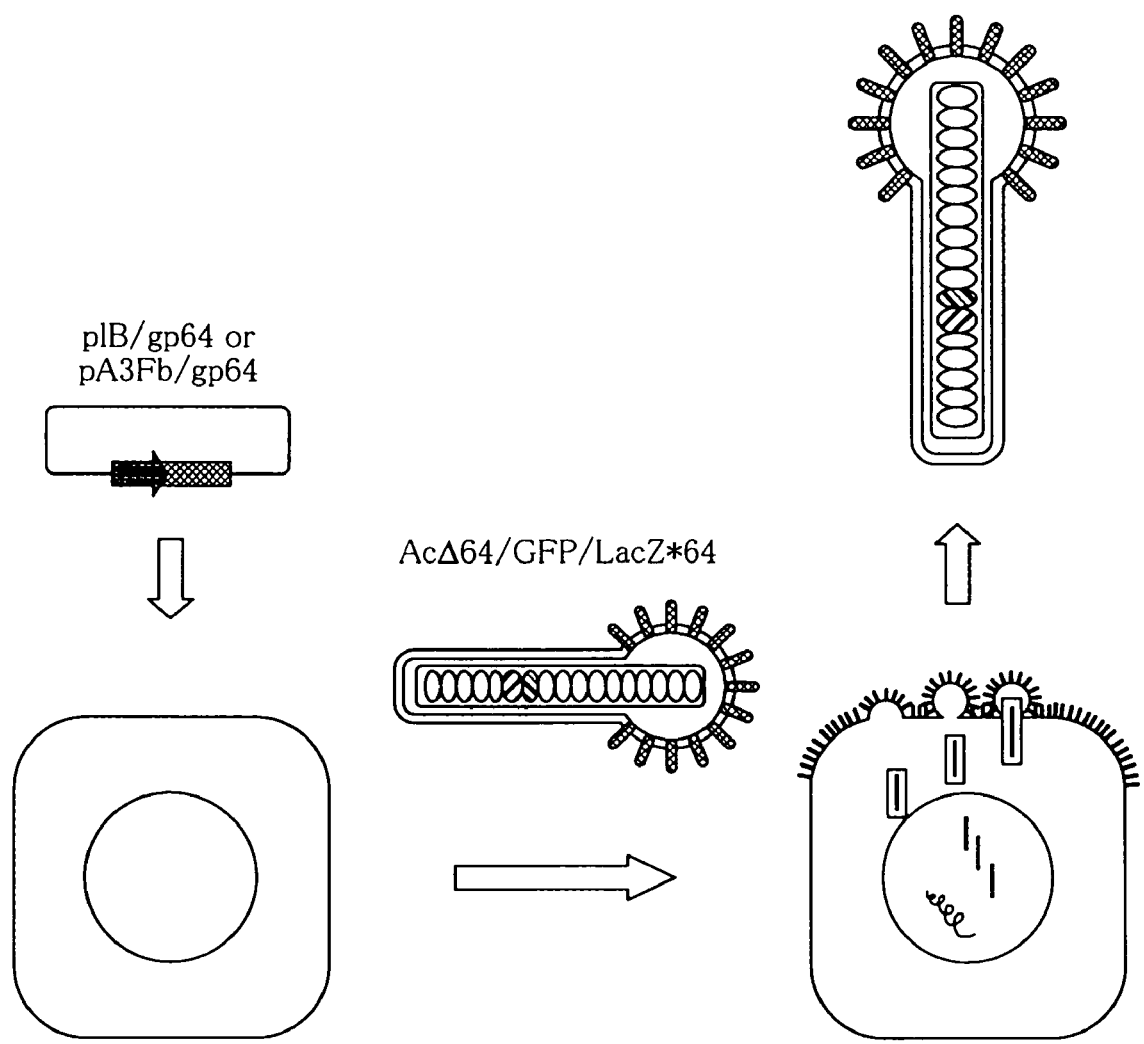

Amplification of AcΔ64/GFP/LacZ*64 (FIG. 12)

The above-isolated AcΔ64/GFP/LacZ*64 is transiently coated with gp64 protein; however, its gp64 has been deleted, so it can infect normal Sf9 cells only once and cannot be amplified. However, virus with a high titer can be easily prepared by infecting Sf9 cells which express gp64 on their surface which have been previously transfected with pIB/gp64 or pA3Fb/gp64.

Example 6

Preparation of Recombinant Virus Expressing Various Kinds of Reporter Genes

In order to allow the transfer gene to be expressed in target mammalian cells, three transfer vectors were used, pAcCAGluc, pAcCAGDsRed and pAcCAGGFP having three kinds of reporter genes, a firefly luciferase gene, red fluorescent protein (DsRed) gene, and GFP gene, respectively, inserted downstream of the CAG promoter. These vectors are designed so that a homologous recombination occurs in the polyhedrin gene region. The preparation of the pAcCAGluc has already been reported (Tani et al., 2001). pDsRed2-N1 (Clontech) was cleaved with KpnI, DsRed gene was collected and inserted into the pAcCAGMCS2 (Shoji et al., 1997) cleaved with the same restriction enzyme to prepare pAcCAGDsRed. pIRES2-EGFP (Clontech) was cleaved with NcoI, the fragment containing GFP was blunted with a klenow fragment, and then cleaved with SmaI and NotI to prepare pAcCAGGFP, having pAcCAGMCS2 blunted with a klenow fragment.

Figure 13:
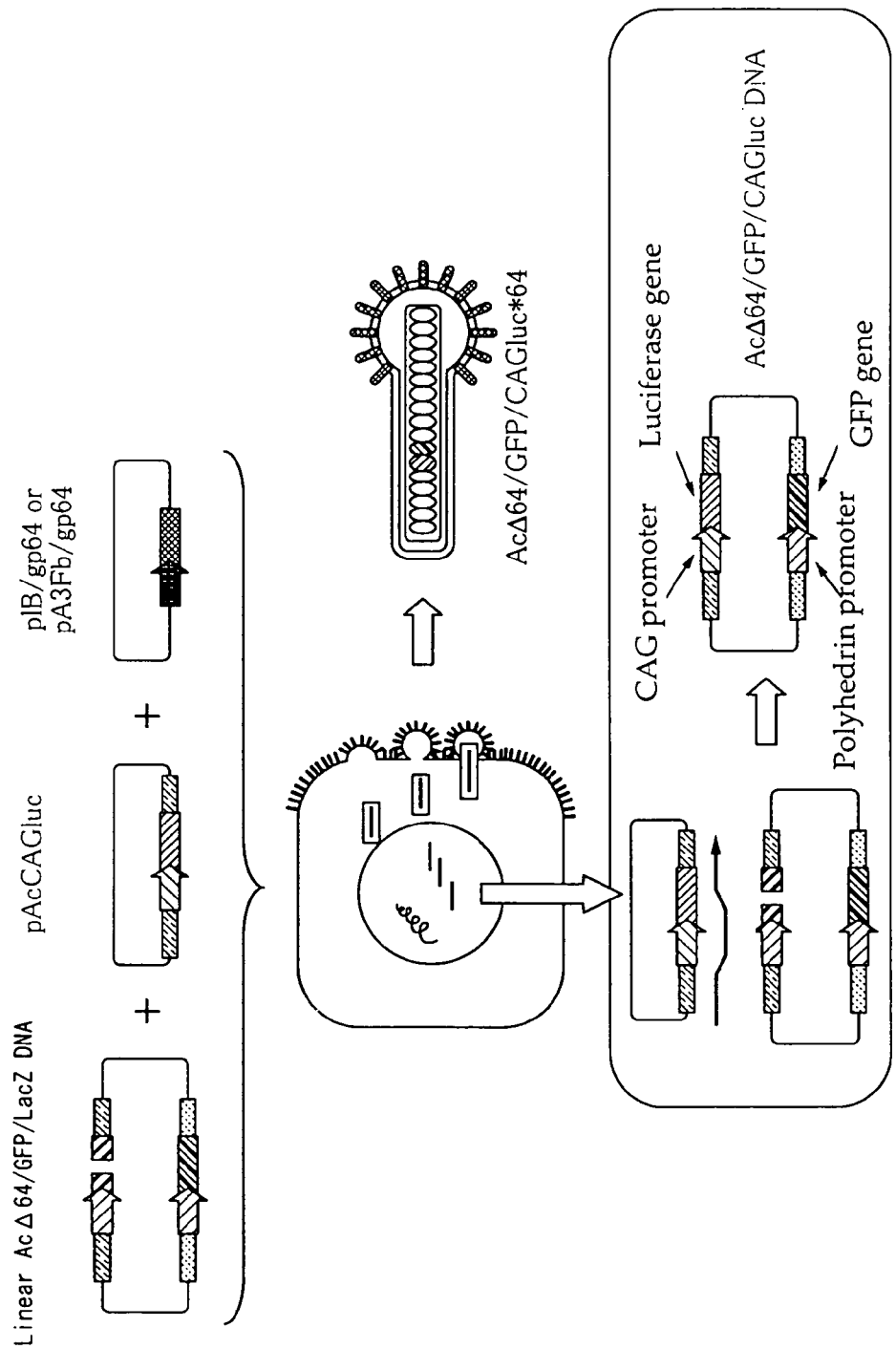
Figure 14:
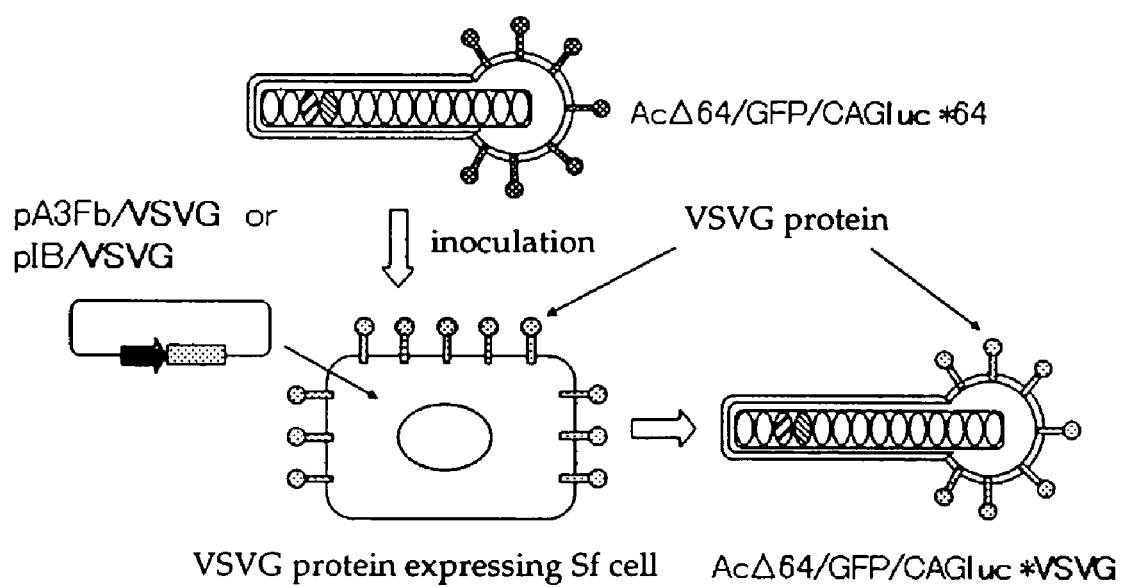
Figure 15:
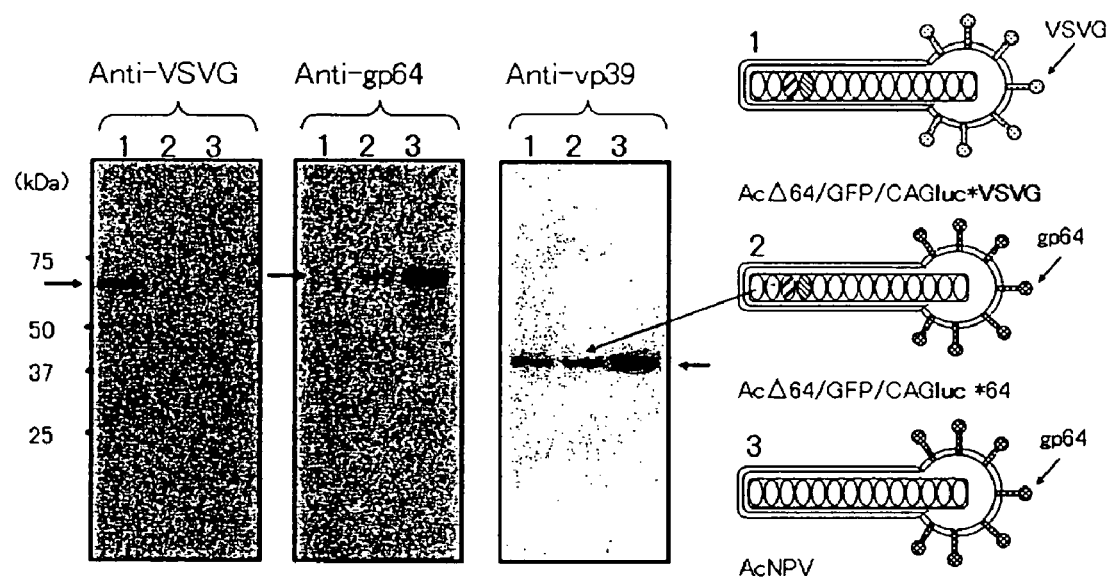
Figure 16:
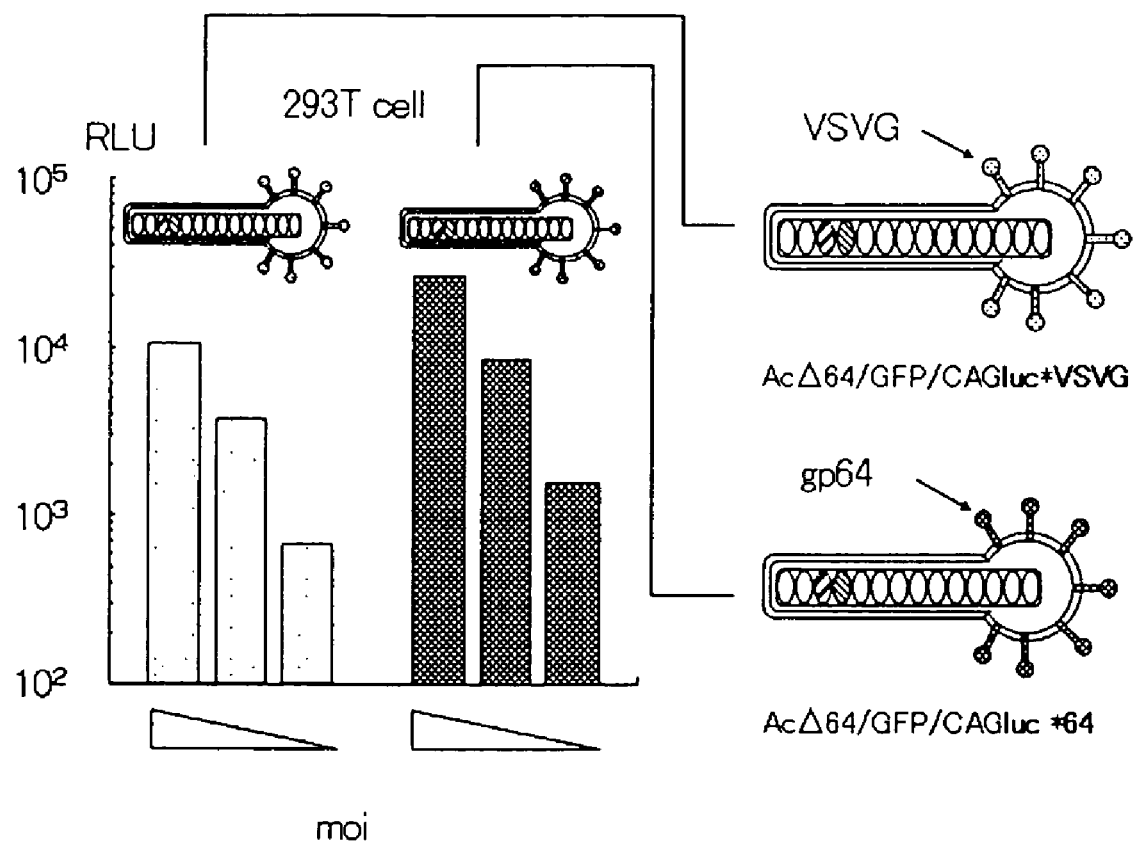
Figure 17A:
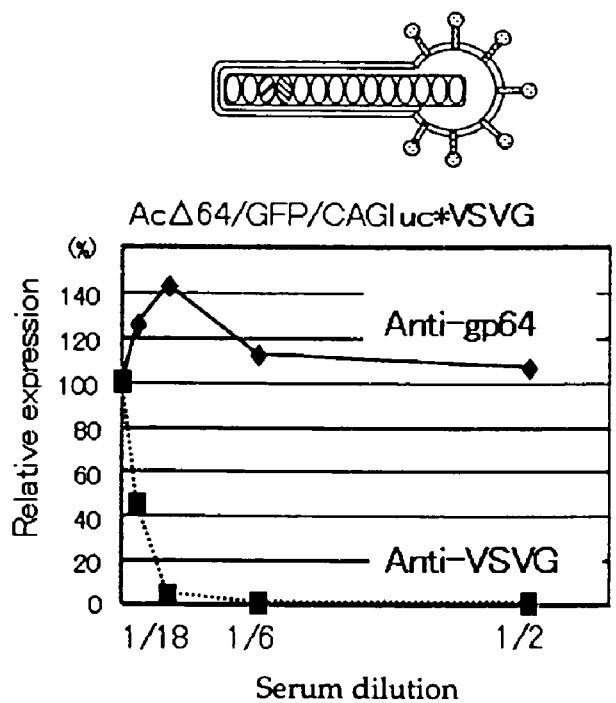
Figure 17B:
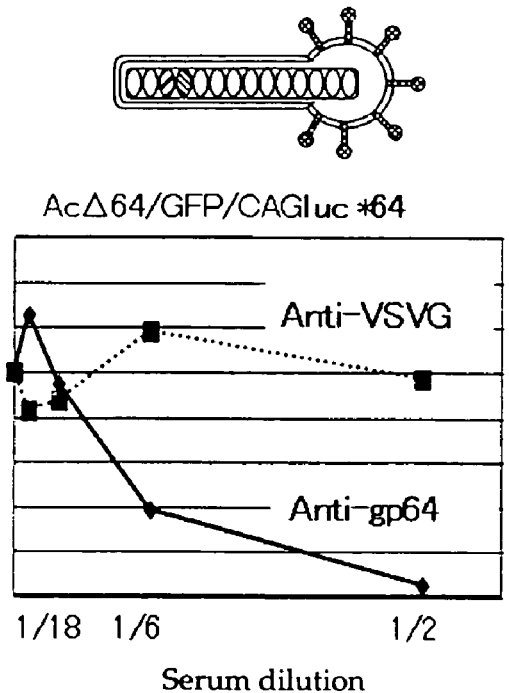

FIG. 13 shows a preparation procedure for recombinant virus using pAcCAGluc. DNA was extracted from AcΔ64/GFP/LacZ*64 and was cleaved at the unique Bsu36I site present in LacZ gene to thereby convert the virus DNA into a linear virus. Sf9 cells were cotransfected with this linear virus DNA, pAcCAGluc, and either pIB/gp64 or pA3Fb/gp64. GFP-positive and LacZ-negative plaques were collected in a similar way. Plaque assays were repeated four times to be purified and recombinant baculovirus AcΔ64/GFP/CAGluc*64 having the luciferase gene was prepared. By infecting Sf9 cells expressing gp64 protein which were transfected with pIB/gp64 or pA3Fb/gp64 beforehand, stock viruses having a high titer were prepared.

Example 7

Preparation of Pseudotyped Virus Coated with Vesicular Stomatitis Virus G Protein (FIG. 14)

The G protein gene of vesicular stomatitis virus was examined as an example of a transgene. pIB/VSVG and pA3Fb/VSVG, where the G protein gene of vesicular stomatitis virus was inserted into pIB/V5-His and pA3Fb, respectively, were prepared. One of these plasmids was transfected into Sf9 cells and after 24 hours, Sf9 cells were infected with AcΔ64/GFP/CAGluc*64 to thereby prepare pseudotyped virus AcΔ64/GFP/CAGluc*VSVG coated with vesicular stomatitis virus G protein instead of gp64 protein. It was confirmed that these viruses were defective in gp64 protein and had the G protein of vesicular stomatitis virus by immunoblotting of purified virus using anti-gp64 antibody and anti-vesicular stomatitis virus antibody (FIG. 15). Further, it was found that the pseudotyped virus AcΔ64/GFP/CAGluc*VSVG transiently coated with the G protein of vesicular stomatitis virus infected a wide variety of mammalian cells efficiently, like the pseudotyped virus AcΔ64/GFP/CAGluc*64 transiently coated with gp64 protein. FIG. 16 shows the results of inoculation of AcΔ64/GFP/CAGluc*64 and AcΔ64/GFP/CAGluc*VSVG, respectively, into 293T cells (obtained from ATCC) at an moi of 10, 30 and 50. Culture supernatant was removed, virus was inoculated, after 60 minutes absorption, medium was added and incubated at 37° C. At 24 to 48 hours postinfection, cells were collected and luciferase gene expression was measured by Bright-Glo luciferase Assay system (manufactured by Promega) and the measurement value is shown.

Further, a neutralization test was performed by neutralizing the AcΔ64/GFP/CAGluc*64 and AcΔ64/GFP/CAGluc*VSVG before cell inoculation using specific antibodies against gp64 and vesicular stomatitis virus G protein (VSVG), respectively (Anti-gp64: anti-gp64 antibody clone #AcV1 (Virology 125, p 432-444 (1983)), Anti-VSVG:anti-VSVG antibody) and by infecting 293T cells. AcΔ64/GFP/CAGluc*VSVG was neutralized well by specific antibody against VSVG (FIGS. 17A and 17B). The neutralization test was performed as follows: the virus vector and antibody were mixed in a dilution concentration shown in horizontal axis of the figure, after 1-hour pre-incubation at room temperature, 293T cells was infected and expression was measured. On the horizontal axis of the figure, the value of ½ represents the concentration where virus vector to antibody is 1:1. Thus it was found that according to the method of producing a baculovirus of the present invention, a baculovirus vector coated with the protein could be propagated. Therefore, it was demonstrated that the desired envelope protein was freely coated regardless of its infectiousness to insect cells. Moreover, according to this method, a very safe baculovirus can be prepared which does not express the envelope protein again after infection of the cell to which the gene is transferred.

Example 8

Preparation of a Baculovirus Expressing Two Proteins on its Particle Surface: a Baculovirus Having Two Envelope Proteins which Determine Host Specificity for Measles Virus Measles is an acute viral infectious disease, which shows strong infectiousness and kills a million people mainly in developing countries every year. Measles virus has two, H and F, envelope proteins on the particle surface and the H protein determines the tissue specificity of infection. Specifically, it is revealed that while a measles virus strain (Edmonston strain) passaged in the laboratory can utilize CD46 or SLAM (Signaling lymphocyte activating molecule; CDw150) as a receptor, a strain freshly isolated from outside utilizes SLAM alone as a receptor. Recombinant baculoviruses expressing H and F proteins on their particle surfaces derived from Edmonston strain or a freshly isolated strain, respectively, were prepared and whether the infection specificity of measles virus can be reproduced in baculoviruses was examined.

A plasmid having the H and F gene of measles virus derived from the Edmonston strain or a freshly isolated strain were integrated instead of pA3Fb/VSVG in Example 7, together with AcΔ64/GFP/CAGluc, was cotransfected to prepare AcΔ64/GFP/CAGluc*MV-H/F. Next, the infection specificity of these baculoviruses were evaluated using a hamster derived cell line (CHO cell) expressing SLAM or CD46. As a result, it was confirmed that the baculovirus vector coated with H and F proteins derived from Edmonston strain infected CHO cells expressing SLAM and CHO cells expressing CD46. In contrast, the baculovirus coated with H and F proteins derived from the freshly isolated strain was capable of gene transfer only into CHO cells expressing SLAM. The positive control virus, AcΔ64/GFP/

CAGluc*VSVG, infected both CHO cell lines, and the negative control virus, AcΔ64/GFP/CAGluc, which is defective in gp64 protein, showed no infectiousness.

This result indicates that two virus proteins can be provided with biological activity retained on the particle surface of baculovirus. It is considered that by providing two proteins on the particle surface, more accurate targeting can be achieved. Moreover, not only providing virus envelope protein, alternatively, by providing virus receptor molecule or single-chain antibody against cancer antigen on the particle surface, suicide genes such as thymidine kinase can be introduced only into cells expressing an envelope protein due to infection with virus or cancer cells and, by using a prodrug in combination, only target cells can be eliminated from the organism. Especially, the AIDS virus infects chronically or persistently, and expresses large amounts of envelope protein on the surface of the infected cells. It is expected that only infected cells will be excluded from the organism by a recombinant baculovirus provided with receptors and co-receptors.

According to the present invention, the problems in conventional technologies can be solved and a novel baculovirus vector which can provide a desired protein which does not have to infect insect cells, on the viral particle surface; a method of producing thereof; and a method of gene transfer using the baculovirus vector, can be provided.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method of producing a baculovirus vector comprising, cotransfecting, and amplifying, wherein said cotransfecting comprises cotransfecting insect cells with at least a plasmid containing a gene coding a first protein capable of being expressed on a cell surface and a recombinant baculovirus DNA, wherein a first pseudotyped baculovirus is generated which comprises at least one part of the baculovirus DNA and which is coated with the first protein capable of being expressed on a cell surface, wherein said amplifying comprises infecting cells which express a plasmid containing a gene coding a second protein capable of being expressed on a cell surface with the first pseudotyped baculovirus; and amplifying the virus DNA to thereby generate a second pseudotyped baculovirus which is coated with the second protein capable of being expressed on a cell surface, and wherein, in the recombinant baculovirus DNA, a polyhedrin gene is replaced with a first foreign gene.

2. A method of producing a baculovirus vector according to claim 1, wherein, in the baculovirus DNA, a gp64 gene is replaced with a second foreign gene.

3. A method of producing a baculovirus vector according to claim 1, wherein, in the process of cotransfecting, a vector containing a second foreign gene is cotransfected at the same time, wherein a gp64 gene in the baculovirus DNA is replaced with the second foreign gene, wherein a pseudotyped baculovirus which comprises the baculovirus DNA containing foreign genes and is coated with the protein capable of being expressed on a cell surface, is generated.

4. A method of producing a baculovirus vector according to claim 1, wherein the first protein capable of being expressed on a cell surface is a protein which renders a baculovirus capable of infecting insect cells when present on the surface of said virus.

5. A method of producing a baculovirus vector according to claim 2, wherein the first foreign gene is at least one of a transgene and a marker gene.

6. A method of producing a baculovirus vector according to claim 2, wherein the second foreign gene is at least one of a transgene and a marker gene.

7. A method of producing a baculovirus vector comprising, cotransfecting, and
amplifying,
wherein said cotransfecting comprises cotransfecting insect cells with at least a plasmid containing a gene coding a first protein capable of being expressed on a cell surface and a wild-type form of baculovirus DNA, a mutant form of baculovirus DNA or a recombinant baculovirus DNA,
wherein a first pseudotyped baculovirus is generated which comprises at least one part of the baculovirus DNA and which is coated with the first protein capable of being expressed on a cell surface,
wherein said amplifying comprises
infecting cells which express a plasmid containing a gene coding a second protein capable of being expressed on a cell surface with the first pseudotyped baculovirus; and
amplifying the virus DNA to thereby generate a second pseudotyped baculovirus which is coated with the second protein capable of being expressed on a cell surface,
wherein the second protein capable of being expressed on a cell surface is a protein which renders a baculovirus incapable of infecting insect cells when present on the surface of said baculovirus.

8. A method of producing a baculovirus vector comprising, cotransfecting, and
amplifying,
wherein said cotransfecting comprises cotransfecting insect cells with at least a plasmid containing a gene coding a first protein capable of being expressed on a cell surface and a recombinant baculovirus DNA,
wherein a first pseudotyped baculovirus is generated which comprises at least one part of the baculovirus DNA and which is coated with the first protein capable of being expressed on a cell surface,
wherein said amplifying comprises
infecting cells which express a plasmid containing a gene coding a second protein capable of being expressed on a cell surface with the first pseudotyped baculovirus; and
amplifying the virus DNA to thereby generate a second pseudotyped baculovirus which is coated with the second protein capable of being expressed on a cell surface,
wherein the baculovirus DNA is a recombinant baculovirus DNA which is defective in its gp64 gene, and
wherein, in the process of cotransfecting, a vector containing a transgene is further cotransfected.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: primer for gp64

<400> SEQUENCE: 1
aaagatctac catggtaagc gctattgttt                                30

<210> SEQ ID NO 2
<211> LENGTH: 30
<212> TYPE: DNA
<213> ORGANISM: Artificial Sequence
<220> FEATURE:
<223> OTHER INFORMATION: primer for gp64

<400> SEQUENCE: 2
ttgtcgactt aatattgtct attacggttt                                30
```